United States Patent [19]

Yuan

[11] 4,305,225

[45] Dec. 15, 1981

[54] HYBRID RICE

[75] Inventor: Long-Ping Yuan, Hunan Province, China

[73] Assignee: China National Seed Corporation, Peking, China

[21] Appl. No.: 156,006

[22] Filed: Jun. 3, 1980

[51] Int. Cl.³ .............................................. A01G 1/00
[52] U.S. Cl. .................................. 47/58; 47/DIG. 1; 111/1; 111/DIG. 1
[58] Field of Search .................... 47/58, DIG. 1, 57.6; 111/1, DIG. 1

[56] References Cited

U.S. PATENT DOCUMENTS 3,102,017 8/1963 Shurter et al. ................. 47/DIG. 1
3,621,612 11/1971 Porter ................................. 47/57.6

Primary Examiner—Robert E. Bagwill
Attorney, Agent, or Firm—Donald W. Erickson; Thomas T. Gordon; Jacqueline S. Larson

[57] ABSTRACT

Methods for the production of seed for growing hybrid rice comprising the planting of rows of male parent seed interspersed with rows of female seed, synchronization of heading and pollination.

11 Claims, No Drawings

HYBRID RICE

This invention relates to improvements in the production of seed for the growing of hybrid rice. In the production of seed for growing hybrid rice in commercial quantities, it is very important to the success of seed formation to synchronize the heading of the male parent and female parent in order to obtain effective pollination of the female. Yuan, Longping, *Zhongao nongyre kexue* (Chinese Agri. Sci.) I, 27–31 (1977).

The present invention is directed at novel improvements in the production of seed for the growing of hybrid rice by improving the synchronization of heading of the parent seed plants and to more effective pollination.

In one aspect of the present invention, seed production is improved by sowing the male parent seed as a mixture of pregerminated seed and dry seed. The term "dry seed" refers to seed which has not been pre-germinated. The delayed sowing of the female seed is then accomplished. The female parent seed is sowed when the leaf number of the male parent is, for example, about 7.5.

In another aspect of the present invention, seed production is increased through improved synchronization of heading by controlling the amount of water in the growing area. If the heading of the male plant is more advanced than the heading of the female plant, water is drained from the growing area. On the other hand, if the heading of the male is less advanced than the female plant, the growing area is flooded deeply. By this method of draining or flooding, the heading can be changed by about 3 to 5 days. The draining or flooding, as the case may be, is maintained until heading of the male and female plants is adjusted as desired and then the amount of water normally present in the growing area is resumed. The time of heading can be predicted up to about 7 to 10 days prior to heading using visual detection methods known in the art. The foregoing method of draining or flooding makes it possible for up to about a 50% adjustment in the time of heading.

In another aspect of the present invention, seed production is increased through improved pollination of the female plant. Pollination can be improved through elongation of the peduncle of the female plant which thereby increases the exposure or accessibility of the flower to pollen. It has been discovered that elongation of the peduncle can be increased advantageously by spraying the top of the female plant with a dilute aqueous solution of gibberellin at a temperature of about 33°–38° C.; preferably 34°–36° C. Generally, a solution containing about 10 to 20 parts per million of gibberellin is used. The temperature of the spray solution when applied should be as close to 35°–36° C. as possible for most advantageous results. The usefulness of the gibberellin treatment is temperature sensitive. A spray solution of higher temperatures may be damaging to the plant. Lower temperatures such as about 20°–30° C. are less beneficial. The spray solution is generally applied in an amount sufficient to provide about 2 to 4 grams of gibberellin per acre. The spray solution is applied to the female plant when the flower head begins to emerge from the leaf sheath. The gibberellin known as gibberellic acid ($GA_3$) can be used satisfactorily in the foregoing method. The gibberellin may be dissolved in solvent such as ethanol prior to make solution.

Herein, the term "male" refers to the "restorer line". Examples of two male varieties which can be used in the production of seed in the practice of the present invention are IR-24 and IR-26. IR is the designation of the International Rice Research Institute, Philippines. Herein, the term "female" refers to the "A line" which is the male sterile line. Examples of female varieties useful in the present invention are Er giu Nan A, Zen San 97A, V-41A and V-20A.

In the growing of seed for hybrid rice in accordance with the present invention, rows of male seed are sowed which are later interspersed with rows of female seed. The male seed is sowed first and the sowing of the female seed is delayed until the leaf number of the male plant is, for example, about 7.5 for Zen San 97A×IR24. The required number of days from sowing of seed to heading is much less for the female than the male. The proximity of the male row to the female rows is important in order to promote effective pollination. Pollen of the male plant is carried to the floret of the female plant by air movement. Thus, the seed grower in determining the orientation of the seed rows and the distance between male rows as well as the spacing of the female rows between the male rows should carefully consider the direction of the wind and average speed of wind at the time of the year when heading of the plants occurs. Advantageously, the rows are sowed perpendicular to the wind direction to promote transmittal of the pollen of the male plant to the female plant. Under moderate wind conditions, a distance of about 140 centimeters between each male row is satisfactory.

If mechanical methods are employed to supplement transmittal of pollen by the natural air movement or wind, the distance may be adjusted accordingly. For example, if an air blower is used to supplement natural wind conditions, the distance between rows may be increased. A distance of about 140 cm. between male rows has been satisfactory for moderate air conditions and if air movement is less than moderate during heading, this relatively short distance lends itself to supplemental pollination methods as by mechanical motion of the male plant through brushing of the male plant by contact with a boom or taut cord. The rows of female seed are sowed parallel and interspersed between the male seed rows. Under moderate conditions, the first row of female seed is sowed about 30 cm. distance from the male row followed by five additional female rows spaced about 16 cm. apart, then another row of male seed and the procedure repeated according to the size of the growing area available. In the use of, for example, IR-24 male seed, the amount of seed sowed can be about 2.5 kilograms per acre. The female seed, such as Er gin nan A, is sowed at the rate of about 7.5 kilograms per acre.

The male seed is sowed as a mixture of pre-germinated seed and dry seed which aids in pollination by reason of extending the number of days during which pollen of the male plant is available. The amount of dry seed in the mixture can vary from about 25 to 75 percent, by weight. A mixture containing 50% dry seed and 50% pre-germinated seed has been found advantageous. Pre-germination of the male seed can be accomplished by soaking the seed in water, draining and then allowing the seed to stand at about 25° to 30° C. until germinated. Depending upon the particular seed, it may require soaking for 2 or 3 days followed by standing at about 30° C. for 1 or 2 days. Thereafter, the pre-germinated seed and dry seed are mixed prior to sowing.

The male and female plants are allowed to grow in the usual way for the local customs or conditions. As the plants approach the heading stage, they are observed carefully in order to predetermine the beginning of the heading stage. The predetermination of the heading stage is done by visual examination as by opening of the leaf sheath in order to predict initiation of the panicle growth using methods known in the art. By predetermining the on-set of the heading stage from one to two weeks prior thereto, it is possible in accordance with the present invention to adjust the on-set of the heading of the male plant so that it is synchronized with the on-set of heading of the female plant. If examination of the plant shows that the on-set of the heading of the male plant is ahead of or earlier than the female plant, then the growing area is drained of water. For example, if the male heading is determined to begin 7 days earlier than female heading, draining or removal of water from the growing area for 7 days will delay heading of the male by about 3 to 4 days. Conversely, if male heading is determined to be later than female heading, increased flooding of the growing area will cause acceleration of the male heading. Flooding to the extent of raising the water level to about 5 to 8 inches above normal level or so that at least the top portion of the plant is exposed—that is, top of the plant is above water level—is used. By use of the draining and flooding method of control of the on-set of male heading, the on-set of heading can be adjusted by about 50 percent. This ability to more closely synchronize heading is very important to the success of pollination. The blooming period generally lasts for about 10 days and through the above method of synchronization of heading, it is possible to synchronize more nearly the blooming of the male and female plants and thereby to maximize the number of days in which the male and female plant blooms co-exist.

An obstacle to efficient pollination in the hybridization of rice is the flag leaf which appears adjacent to the peduncle. This obstacle can be overcome by removal of the flag leaf as by cutting, by spraying the top of the female plant with a warm aqueous solution of gibberellin to promote growth of the peduncle or by a combination of the two methods. For most efficient pollination, the flag leaf is removed followed by spraying the female plant with gibberellin solution. The spraying is not harmful to the male plant. The warm gibberellin solution is sprayed on the top of the female plant at the time when the floret is beginning to appear out of the leaf sheath. It promotes elongation of the top inter node (peduncle) and hence more efficient pollination by reason of increased accessability of the floret to pollen of the male plant.

Following pollination, it is preferred and good practice to remove rogue or non-typical plants which may occur randomly. This practice, although not necessary, improves the purity of the desired hybrid seed.

In the harvest of the seed, it is good practice to harvest the male (restorer) seed first in order to minimize the presence of the restorer seed, in the desired hybrid seed.

What is claimed is:

1. In a process for the production of seed for growing hybrid rice, the improvement which comprises sowing the male parent seed as a mixture of pre-germinated seed and dry seed, said mixture containing from about 25% to 75% of the dry seed, by weight.

2. The improvement according to claim 1 wherein the mixture contains about 50% of dry seed.

3. In a process for the production of seed for growing hybrid rice, the improvement wherein the on-set of heading of the male plant is adjusted by draining of water from the growing area or flooding of the growing area by raising the level of the water.

4. The improvement according to claim 3 wherein the on-set of heading is delayed by draining of water from the growing area.

5. The improvement according to claim 4 wherein said water is drained within seven to ten days prior to the on-set of heading.

6. The improvement according to claim 3 wherein the on-set of heading is advanced by raising the water level in the growing area.

7. The improvement according to claim 6 wherein said flooding is made within seven to ten days prior to the on-set of heading.

8. In a process for the production of seed for growing hybrid rice, the improvement which comprises spraying the female plants with a warm solution of gibberellin at about the time that the flower begins to emerge from its leaf sheath, said solution having a temperature of about 34° to 38° C.

9. The improvement according to claim 8 wherein the solution is a dilute aqueous solution and the temperature is 35°–36° C.

10. The improvement according to claim 8 wherein the gibberellin is gibberellin $GA_3$.

11. The process according to claim 8 wherein the improvement includes removal of the flag leaf.

* * * * *